US005614559A

United States Patent [19]
Singh et al.

[11] Patent Number: 5,614,559
[45] Date of Patent: Mar. 25, 1997

[54] COMPOUND FOR INHIBITING HIV INFECTIVITY

[75] Inventors: Shyam K. Singh, Arlington; Raymond J. Patch, Framingham; Peter V. Pallai, Westwood; Edith A. Neidhardt, Boxford; Gerard P. Palace, Waltham; Kevin J. Willis, Newton; Theresa M. Sampo, Watertown, all of Mass.; Kevin W. McDonald, Merrimack, N.H.; Zhan Shi, Waltham, Mass.

[73] Assignee: Procept Inc., Cambridge, Mass.

[21] Appl. No.: 245,619

[22] Filed: May 19, 1994

Related U.S. Application Data

[63] Continuation-in-part of Ser. No. 156,443, Nov. 23, 1993, abandoned.

[51] Int. Cl.⁶ .................. A61K 31/185; C07C 309/35; C07C 309/32
[52] U.S. Cl. .................. 514/577; 514/576; 514/764; 514/765; 514/766; 562/88; 562/89
[58] Field of Search .................. 514/765, 766, 514/494, 576, 577, 764; 562/88, 89

[56] References Cited

U.S. PATENT DOCUMENTS

| | | | |
|---|---|---|---|
| 4,361,547 | 11/1982 | Sipos et al. | 424/56 |
| 4,604,404 | 8/1986 | Munson, Jr. et al. | 514/494 |
| 5,177,083 | 1/1993 | Rideout et al. | 514/296 |
| 5,308,612 | 5/1994 | Lee | 424/78.35 |

FOREIGN PATENT DOCUMENTS

| | | |
|---|---|---|
| 0384532 | 8/1990 | European Pat. Off. |
| 2669535 | 5/1992 | France |
| WO92/12709 | 8/1992 | WIPO |
| 93/14146 | 7/1993 | WIPO |
| WO94/03164 | 2/1994 | WIPO |
| WO94/14763 | 7/1994 | WIPO |

OTHER PUBLICATIONS

Taylor, D.L. et al., "Novel Sulphonic Acid Polymers as Inhibitors of HIV Host–Cell Interactions," Abstract PO–B26–2071, *IXth International Conference on Aids*, Jun. 6–11, 1993.

Tan, Ghee T. et al., "Sulfonic acid polymers are potent inhibitors of HIV-1 induced cytopathogenicity and the reverse transcriptases of both HIV-1 and HIV-2," *Biochimica et Biophysica Acta*, 1181:183–188 (1993).

Mohan, Prem et al., "Sulfonic acid polymers as a new class of human immunodeficiency virus inhibitors," *Antiviral Research*, 18:139–150 (1992).

*Primary Examiner*—Peter O'Sullivan
*Attorney, Agent, or Firm*—Hamilton, Brook, Smith, Reynolds, P.C.

[57] ABSTRACT

This invention pertains to the discovery that condensation polymers of an aldehyde and aromatic sulfonic acids and fractions thereof, such as formaldehyde naphthalene-sulfonic acid condensation polymers, can abrogate HIV gp120 binding to CD4, as demonstrated in CD4/gp120 binding assays. In addition to gp120 binding inhibition, the compounds have been shown to inhibit HIV-induced syncytia formation and infectivity of CD+ cells. The use of this compound has been shown to be non-cytotoxic and non-inhibitory to antigen induced T lymphocyte proliferation. Based on these findings, these compounds can be used as a therapeutic agent for the treatment of acquired immunodeficiency syndrome (AIDS), as well as AIDS-related complex (ARC), AIDS-related dementia and non-symptomatic HIV infection. The compounds can also be used to treat blood preparations.

39 Claims, 4 Drawing Sheets

COMPOUND FOR INHIBITING HIV INFECTIVITY

RELATED APPLICATION

This application is a continuation-in-part of U.S. application Ser. No. 08/156,443 filed Nov. 23, 1993, now abandoned the entire teachings are incorporated by reference herein.

BACKGROUND OF THE INVENTION

CD4, a surface glycoportein protein receptor found on a subset of T lymphocytes known as CD4+ cells, is involved in Class II major histocompatibility complex (MHC) recognition and appears to be the physiological receptor for Class II MHC. Human CD4 is also the receptor for the gp120 envelope glycoprotein of the human immunodeficiency virus (HIV) and is essential for virus entry into the host cell, and for membrane fusion, both of which contribute to cell-to-cell transmission of the virus and to its cytopathic effects. It is known that HIV causes AIDS by attacking the immune system and destroying CD4+ cells, thus leaving the body defenseless against attack by bacterial and other viral pathogens. CD4 has been shown to be the major route of entry of HIV into CD4+ cells by binding to CD4.

Considerable effort has been expended in studying the CD4/gp120 interaction and in trying to interfere with or inhibit that interaction, in an attempt to provide a means by which the life threatening effects of HIV infection can be slowed or reversed. Thus far, a small number of antiviral drugs have been developed to interfere with infection of cells by HIV and its subsequent effects, such as zidovudine (also known as AZT) or dideoxyinosine (ddI). A means by which to prevent HIV infection of CD4 bearing lymphocytes, which make up approximately 60–80% of the total circulating T lymphocyte population, would be of great value, particularly in light of the fact that HIV infection of such cells can cause total collapse of the immune system and would be expected to avoid development of a viral resistance to the therapy. One compound, dextran-sulfate, was discovered to interfere CD4/gp120 interaction. However, the compound resulted in unacceptable levels of anti-coagulation activity. It would be of further value to develop agents that can be used to treat CD4-related diseases such as AIDS-related complex (ARC), AIDS-related dementia and non-symptomatic HIV infection which avoid significant levels of anti-coagulation activity.

Many condensation polymers of formaldehyde and aromatic sulfonic acids have been previously described. U.S. Pat. No. 4,604,404 discloses the use of some such polymers as antiviral agents against the Herpes simplex virus. However, the reference does not teach or suggest the use of such compounds in the treatment of HIV infections and related diseases and conditions.

SUMMARY OF THE INVENTION

This invention relates to the discovery that condensation polymers of aromatic sulfonic acids and an aldehyde and fractions thereof, particularly naphthalenesulfonic acid formaldehyde polymers (such as PRO 1041 and PIC 024.4, and fractions thereof defined below) can abrogate HIV gp120 binding to CD4, as demonstrated in CD4/gp120 binding assays. Compounds of the present invention have been shown to be non-cytotoxic and non-inhibitory to antigen induced T-lymphocyte proliferation and exhibit specificity as manifested by lack of inhibition in CD2/LFA-3 (lymphocyte function-associated antigen) (CD58) binding assay. Based on these findings, condensation polymers of aromatic sulfonic acids and an aldehyde and fractions thereof can be used as therapeutic agents for the treatment of acquired immunodeficiency syndrome (AIDS), as well as AIDS-related complex (ARC), AIDS-related dementia and nonsymptomatic HIV infection. The compounds can also be used to treat a blood preparation in vitro to prevent HIV infection of CD4 +cells present in the blood preparation.

DETAILED DESCRIPTION OF THE INVENTION

Figure 1:
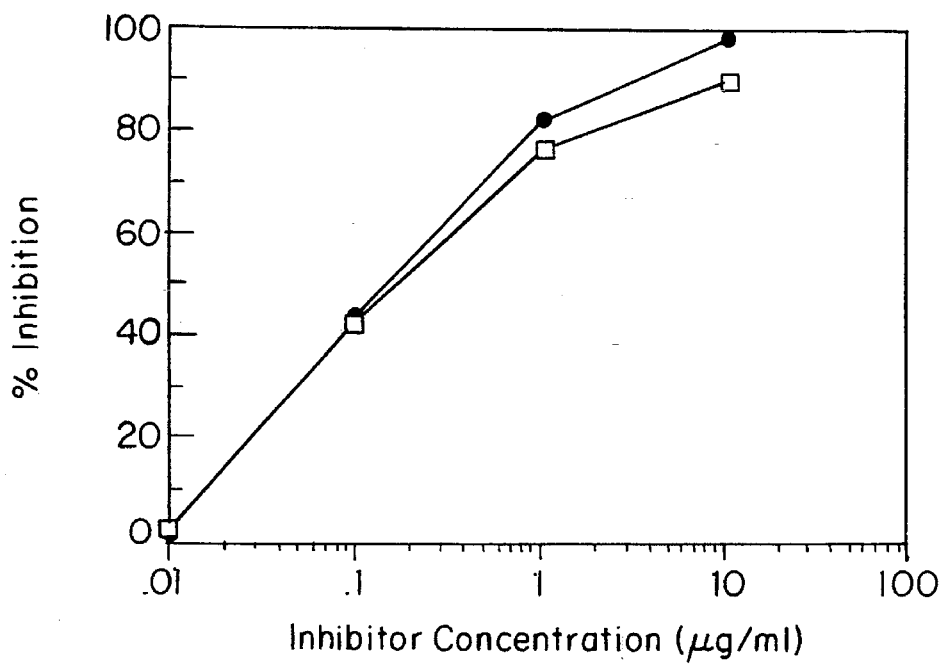
FIG. 1 is a graph of the inhibition of gp120 binding to immobilized soluble CD4 (sCD4) by PIC 024.4 (designated by an open square) and PRO 1041 (designated by a closed circle).

The preparation of aldehyde condensation polymers of aromatic sulfonic acids is well known in the art. Aromatic sulfonic acids, as employed herein, include aromatic carbocyclic and heterocyclic rings substituted by one or more sulfonic acid moieties. Aromatic carbocyclic rings include phenyl, naphthyl, tetrahydronaphthyl, biphenyl, phenylalkylphenyl, phenylalkenylphenyl, phenoxyphenyl, phenylthiophenyl and phenoxyalkoxyphenyl, for example. Aromatic heterocyclic rings include, pyridinyl, pyrimidinyl, quinolinyl, thiophenyl, furanyl, pyrazolyl, imidazolyl, pyrrolyl and thiazolyl, for example. Aldehydes useful in the preparation of compounds for the present invention include formaldehyde, acetaldehyde, propionaldehyde and benzaldehyde, for example. Preferably, the aldehyde is formaldehyde. The term "polymer", as employed herein, includes any compound formed by the coupling of two or more monomers or repeating units. U.S. Pat. 4,604,404 exemplifies suitable polymers useful herein and methods of preparing them, the teachings therein being incorporated by reference.

One such compound, a condensation polymer of formaldehyde and naphthalenesulfonic acid, can alternatively be isolated from dye compositions such as Direct Yellow 29, a commercial dye comprising a mixture of several compounds wherein the compound of interest was added as a dispersant. Prior to formulation in a suitable physiologically acceptable vehicle, the preparation can be purified using known purification techniques, such as precipitation, crystallization, extraction and/or chromatography to isolate PIC 024.4. An example of the latter of these is described in detail in the exemplification.

The condensation polymers employed herein can, optionally, be fractionated to obtain a narrow or mono-dispersed molecular weight condensation polymers.

In general, as the molecular weight of the polymer increases, the therapeutic activity of the compound increases. However, the anticoagulation activity of the compound also increases as the molecular weight increases. Accordingly, the molecular weight is advantageously chosen to achieve optimal antiviral activity while minimizing the anticoagulation effect.

The compound can be selected which achieves a preferred therapeutic ratio. "Therapeutic ratio" is defined herein as the dosage (μg/ml) required to achieve an average anticoagulation doubling time of the upper normal partial thromboplastin time, employing the anticoagulation assay set forth below, divided by the dosage (μg/ml) required to achieve fifty percent inhibition of CD4-gp120 binding in the cellular assay, set forth below. The preferred therapeutic ratio is at least about 7, most preferably at least about 20.

It is preferred that the peak molecular weight ($M_p$) be less than about 50 kDa and/or greater than about 0.7 kDa. More preferred are polymers with a peak molecular weight between from about 1.3 to about 30 kDa, most preferred between from about 4 to about 12 kDa. Preferably, the average number of sulfonic acids per aromatic group is between about 0.5 to about 2.0, most preferably about 1.0.

The narrow or mono-dispersed molecular weight polymers can be prepared by fractionation methods known in the art (see, e.g., *Polymer Fractionation*, Editors, Cantow and Manfred, Jr., (Acad. Press) 1967), such as solvent precipitation, gel permeation chromatography, salt precipitation and difiltration. Alternatively, the polymers can be manufactured by the stepwise or controlled condensation of naphthalenesulfonic acid and formaldehyde.

PIC 024.4 abrogated CD4/gp120 binding in a primary binding assay. The compound showed antiviral activity against HIV strains HTLV-IIIB, JR-CSF and ADA in in vitro assays. Furthermore, the compound was found to be specific and non-cyto-toxic as it failed to show activity against CD2/LFA-3 interaction and T-cell proliferation or toxicity against a variety of cell lines tested. From this data, more specifically set forth below, it is concluded that condensation polymers of the type herein described are active as antiviral agents against the virus, HIV.

Based upon the results discussed herein, a preparation containing condensation polymers of formaldehyde and aromatic sulfonic acids, such as PRO 1041 and PIC 024.4, can block all CD4 mediated steps of HIV infection. As such they can be used to treat individuals infected with HIV, in vivo (e.g., by administration to infected individuals). The compounds are active against CD4-mediated infection by non-syncytia inducing (NSI) and syncytia inducing (SI) phenotypes of the HIV virus. It can also be used prophylactically for uninfected individuals (such as needle stick accidents and in transfer from mother to newborn) and individuals who test positive for HIV antibodies but remain asymptomatic. The preparation can be used to inhibit binding of HIV to CD4 lymphocytes and to inhibit transmission of virus from an infected cell to uninfected cells including HIV infection mediated by syncytia formation. As the compound inhibits the binding of HIV to CD4, and is an immune system specific intervention, it is not expected to lead to viral resistance.

The condensation polymer can, optionally, be administered as a pharmaceutically acceptable salt. Examples of suitable salts include the alkaline, alkali metal and ammonium salts, such as calcium, sodium and ammonium salts.

The preparation of this invention can be administered intravaginally or rectally (e.g., contraceptive formulation or suppository), orally (e.g., capsule, tablet or liquid formulation), parenterally (e.g., intra-muscularly, intravenously, subcutaneously), topically, nasally or via slow releasing microcarriers in dosage formulations containing a physiologically acceptable vehicle and optional adjuvants and preservatives. Suitable physiologically acceptable vehicles include saline sterile water, Ringer's solutions, and isotonic sodium chloride solutions. Specifically, Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP can be used, for example. Advantageously, the compounds can be administered in a contraceptive formulation, such as a contraceptive gel, cream or foam. The specific dosage level of active ingredient will depend upon a number of factors, including biological activity of the particular preparation, age, body weight, sex, general health and the clinical stage of AIDS.

Other antiviral agents which interfere with HIV viral replication can be administered in conjunction with this preparation, according to the methods of this invention. Co-administration of antiviral agents can effectively inhibit various stages of the virus life cycle, thus optimizing the therapeutic benefit of the preparation of this invention, for reducing or eliminating viral infectivity and the symptoms associated therewith. For example, an HIV reverse transcriptase inhibitory agent, such as zidovudine (AZT) or dideoxyinosine (ddI), or an HIV protease, or a non-nucleoside inhibitor such as nevirapin can be co-administered with the condensation polymer separately or as a single dosage formulation containing the condensation polymer and other anti-viral agent(s).

Additionally, the compound can be added to a blood preparation in vitro. In this embodiment the compound effectively blocks viral binding and entry into $CD4^+$ cells, preventing infection of T-cells. The compound can be added to the blood preparation alone or in combination with a suitable vehicle, such as saline sterile water, Ringer's solution or isotonic sodium chloride solutions, for example. The effective amount required will depend upon a number of factors, including the particular blood preparation, and the vehicle chosen.

The invention will be further illustrated by the following non-limiting exemplification:

Isolation and Characterization Of PIC 024.4

A solution of Direct Yellow 29 (Aldrich Chemical Company, lot #0033187; Sigma Chemical Company, lot

17F3484), was prepared by dissolving 10.0 g in 200 ml of water, the solution was acidified with trifluoroacetic acid (0.1% trifluoroacetic acid final concentration) and stirred for one hour at 4° C. The precipitate was removed by filtration and the filtrate was subjected to preparative high pressure liquid chromatography (HPLC) using a Waters 600E system equipped with PrePak®RCM cartridge column assembly (Waters Chromatography, Division of Millipore, Milford, Mass.). The mobile phase consisted of 0.1% trifluoroacetic acid in water (solvent A) and 0.1% trifluoroacetic acid in acetonitrile/water (60:40) (solvent B). With an initial solvent mixture of 70% solvent A; 30% solvent B and a flow rate of 25 ml/min, the stock solution (5 ml) was loaded onto a 40 ×300 mm DeltaPak™ $C_{18}$ column (particle size =15 μm, mean pore diameter =300 A). The concentration of solvent B was increased to 70% at a rate of 1.2%/min and then to 100% at a rate of 15%/min. Monitoring at 280 nm, the material eluting between 10.0 and 21.8 minutes was collected and concentrated to afford PIC 024.4.

PIC 024.4 was characterized by a variety of techniques such as HPLC, NMR, IR, UV and fluorescence determinations.

$^1$H NMR spectrum (250 MHz Bruker, DMSO-$d_6$) of PIC 024.4 was comprised of the following peaks: δ6.5–8.6 (br m), 4.8–5.0 (br s), 4.2–5.0 ppm (br s).

In the IR of PIC 024.4 (FT, Perkin Elmer, KBr), 3448, 1630, 1400, 1186, 1122, 1030 and 680 cm$^{-1}$ were the main peaks.

Synthesis of Condensates: Polymerization

A mixture of 2-naphthalenesulfonic acid sodium salt (1.15 g, 5 mmol), 37% aqueous formaldehyde (0.65 ml, ~6 mmol), and sulfuric acid (0.7 g concentrated sulfuric acid in 0.5 ml of water) was heated at 98° to 100° C. for 43 hours. The reaction mixture was then diluted with water (30 ml), neutralized with calcium carbonate to pH 7 and filtered, the filtrate was evaporated to dryness to yield 1.22 g of the condensate PRO 1041.

$^1$H NMR and IR of this product was found to be similar to PIC 024.4 reported above.

The above experiment was repeated modifying the reaction parameters as exemplified in Table 1.

addition of ice (~100g). Before the ice completely dissolved, 20 ml of 40% HBr aqueous solution was added dropwise and the resulting suspension was maintained at −5° to 0° C., then 10 ml of NaNO$_2$ (3.65 g) aqueous solution was added in 30 minutes. The mixture was stirred continuously for 30 minutes at −5°~0° C. The unreacted NaNO$_2$ was decomposed by addition of 350 mg of urea at the end of reaction. The resulting dark diazonium suspension was kept below 0° C., and added dropwise over one hour period to CuBr (7.15 g) solution in 40 ml of 40% HBr at 70° C. with vigorous stirring (the CuBr solution was in a 1000 ml flask). The dark mixture was stirred at 80° C. for 40 minutes, then cooled down to room temperature and added with 200 ml of water. The precipitate was collected in Buchner funnel and washed with about 50 ml of water. 13.9 g of crude product was obtained after drying under vacuum. The crude compound was refluxed in 500 ml of water for 2 hours, cooled to room temperature and filtered. The filtrate was evaporated to dryness and solid dried in vacuo to yield 8.23 g (57% yield) of pure product.

The purity of product was checked with reverse phase HPLC and $^1$H-NMR (250 MHz).

8, 8'-Methylen-bis-5-bromo-2-naphthalenesulfonic acid (sodium salt)

A mixture of 5-bromo-2-naphthalenesulfonic acid (17.22 g), TFA (200 ml), Amberlyst-15 resin (17 g, heated at 130° C. for 14 hours in a closed thick-wall tube. After cooling to room temperature, the mixture was filtered in a Buchner funnel and, the collected solid was washed with about 10 ml of TFA, dissolved in 250 ml of methanol/water (4/1) and filtered. The filtrate was evaporated to dryness and the solid was suspended in 80 ml of water, neutralized to pH~8 with 10 M NaOH. The solid was filtered, washed with 60 ml of acetone and dried in vacuo overnight. 15.03 g (80% yield) of pure product was obtained.

8,8'-Methylen-bis-2-naphthalenesulfonic acid

A suspension of 8,8'-methylen-bis-5-bromo-2-naphthalenesulfonic acid (sodium salt, 6.30 g), NaOH (0.32 g) in 300 ml of MeOH, was slowly added with Pd—C (10%, 5.0 g) under argon atmosphere. The suspension was shaken at 50 psi of H$_2$ for 18 hours. Then the mixture was filtered and the

TABLE 1

| Reaction | HCHO (eqv) | Water (ml) | Temp (°C.) | Time (h) | Product size (kDa) | | |
|---|---|---|---|---|---|---|---|
| | | | | | Mp | MWd | MW |
| PRO 1041* | 1 | 0.5 + 1 | 96–104 | 45 | 6.0 | 0.7–150 | 16 |
| PRO 1077* | 1 | 1.5 + 0.5 | 103–107 | 52 | 25 | 0.2–100 | 13 |
| PRO 1078* | 1 | 2 + 0.5 | 100–103 | 54 | 2.0 | 2–200 | 12 |
| PRO 1079* | 1 | 2 + 1 | 100–105 | 44 | 0.4 | 0.3–175 | 9 |
| PRO 1080 | 1 | 1.5 | 95–100 | 44 | 2.0 | 0.4–90 | 9 |
| PRO 1081 | 1 | 1.5 | 100–105 | 53 | 4.0 | 0.4–100 | 14 |
| PRO 1082 | 1 | 2 | 105–110 | 92 | 8.0 | 3–100 | 14 |
| PRO 1083 | 1 | 0.5 | 96–105 | 72 | 21 | 0.1–980 | 56 |
| PRO 1121 | 1 | 1.5 | 120–125 | 6 | 0.2 | 0.2–10 | 2 |
| PRO 1122 | 1 | 1.5 | 120–125 | 8 | 0.2 | 0.3–15 | 2 |
| PRO 1133 | 1 | 1.5 | 120–125 | 15 | 3.0 | 0.3–100 | 4 |
| PRO 1135 | 1 | 1.0 | 120–125 | 8 | 3.0 | 0.4–80 | 14 |
| PRO 1075 | 0.5 | 1.5 | 98–100 | 48 | 3.0 | 0.4–100 | 11 |
| PRO 1076 | 0.75 | 1.5 | 98–100 | 24 | 4.0 | 1–120 | 18 |

*Open vessel reactions; Mp = peak molecular weight; MWd = molecular weight distribution; MW = molecular average weight Synthesis of Condensates: stepwise 5-Bromo-2-naphthalenesulfonic acid 5-Amino-2-naphthalenesulfonic acid (11.15 g, 50 mmol) was dissolved in 100 ml of 0.5 N NaOH solution with stirring. The dark-red solution was cooled down to 0° C. by filtrate was passed through a column packed with ~20 g of IR-120 resin. The solvent was removed on rotavap, and the residue was dissolved in 200 ml of water then filtered again. The filtrate was neutralized with 5 M NaOH to pH ~7 and concentrated to ~50 ml volume, then 300 ml of acetone was added slowly with shaking. The resulting white precipitate was collected in Buchner funnel, washed with 20 ml of acetone and dried in vacuo to result 3.51 g of dry product (sodium salt).

Oligomerization for Tetramer and Hexamer 5.11 g of sodium salt of dimer was converted into free acid by passing through IR-120 resin column in water. Water was removed on rotavap and the residue was again dissolved in 10 ml of water and transferred into 50 ml of TFA in a thick-wall flash, then paraformaldehyde (0.195 g) was added and the flask was sealed. The solution was stirred at 60° C. –65° C. for 15 hours. The solvent was removed and the residue was dissolved in methanol, coated on silicon gel and subjected to flash silicon-gel column (EM Science, silica gel 60 F–254, 230–400 mesh for column), where the elution was started with 16:1:1 of THF:MeOH:$H_2O$ to 5:1:1 final ratio.

The solid from tetramer fraction was neutralized to pH ~7 with 5 M NaOH in 5 ml of water, added with 5 ml of MeOH and 125 ml of acetone to afford 0.94 g of precipitate. The salt was converted into free acid by passing through IR-120 resin and 0.73 g of dry tetramer was obtained.

From the hexamer fraction 0.21 g of hexamer was obtained by the same method as that described for tetramer.

3.5 g of starting material (dimer) was recovered from the first fraction.

Octamer

A mixture of tetramer (130 mg), Amberlyst-15 resin (150 mg), water (0.4 ml), and 2 ml of TFA solution of paraformaldehyde (1 mg/ml) was stirred at 85° C. for 15 hours in a sample vial closed with a teflon cap. The reaction mixture was cooled to room temperature, diluted with 5 ml of water and filtered. The filtrate was evaporated to dryness, dissolved in methanol, and coated on silica gel, then passed through a flash column where tetramer was eluted with 6:1:1 of THF:isopropanol:$H_2O$, and octamer was eluted with MeOH:$H_2O$ (85/15). From later fraction 50 mg of crude octamer was obtained.

The crude octamer was passed through IR-120 resin, purified by reverse phase prep HPLC and 15 mg of octamer (96.6% pure by analytical HPLC) was obtained.

Reverse Phase High Pressure Liquid Chromatograph (RPHPLC):

PIC 024.4 and PRO 1041 were subjected to analytical HPLC using a Waters 625 pump/490 detector/Satellite WISP system equipped with a Zorbax RX-C18 column (4.6 ×150 mm, 5 μM particle size, 90A pore size) (MAC-MOD Analytical, Chadds Ford, PA). The mobile phase consisted of 0.1% trifluoroacetic acid in water as solvent A and 0.1% tri-fluoroacetic acid in acetonitrile/water (60:40) as solvent B. The samples were injected at an initial solvent mixture of 90% solvent A: 10% solvent B and a flow rate of 1 ml/min. The concentration of solvent B was increased to 100% at a rate of 2.5%/min. and elution monitored at 233 nm. PIC 024.4 and PRO 1041 exhibited similar chromatographic profiles.

UV Absorption Spectra

UV spectra were recorded at 20° C. over the wavelength range 200 to 350 nm, with a spectral resolution of 1 nm, for both samples of PRO 1041 and PIC 024.4 at concentrations of approximately 2μg/ml, in phosphate buffered saline (PBS), pH 7.4. The spectrophotometer was a Perkin Elmer Lambda 6 and a 1 cm pathlength cuvette was used.

The spectra for both PRO 1041 and PIC 024.4 had a maximum at 228 nm. Smaller bands at 296 nm with shoulders at 330 nm where also present in the spectra of both compounds.

Fluorescence Spectroscopy

Fluorescence emission spectra were recorded at 20° C. over the wavelength range 320 nm to 500 nm with a spectral resolution of 2 nm for both samples of PRO 1041 and PIC 024.4 in PBS at a concentration of approximately 2μg/ml. The spectrofluorimeter was a SLM-Aminco SPF500C and the excitation wavelength was 300 nm having a bandpass of 4 nm. A 0.5 cm pathlength cuvette was used and the volume was 500 μl.

PRO 1041 and PIC 024.4 had closely similar emission spectra having a maximum intensity at ~355 nm.

Size Exclusion Chromatography

Aliquots of synthetic polymer solutions were fractionated by size using a Waters M625 pump, M996 diode array detector, Millenium software system and either two 6 μm 250 angstrom Waters Ultrahydrogel columns (7.8×300 mm; mobile phase flow 1 ml/min) or a 17 μm TosoHaas G3000 PW column (21.5×600 mm) coupled with a TSK-Gel Guard PWH column (21.5×75 mm; flow rate 3 ml/min). The mobile phase consisted of 0.2 M ammonium acetate (pH 6.2) made from glacial acetic acid (Baker Analyzed HPLC Reagent) and ammonium hydroxide (25%, Mallinckrodt)- and 35% acetonitrile (B&J Brand). Prior to use, the mobile phase was filtered through a 0.45 μm nylon membrane and sparged under Grade 5 helium. A solution of the synthetic samples at 2.2–10 mg in up to 200 μl MilliQ water was injected onto the Ultrahydrogels or 40–300 mg in up to 2 ml MilliQ watermobile phase (50:50, v/v) was injected onto the TosoHaas columns following ultrasonicating (Branson 2200), vortexing and filtering (0.45 μm Acrodisc, Gelman Sciences). Collected fractions were pooled according to elution time. Superimposable chromatographic profiles by absorbance measurements were demonstrated with replicates- and the solvent was removed using Savant speed-vacs at high temperature (either SC200 and Vapornet VN100 or Plus SC210A). The residue was redissolved in water and redried for removing trapped solvent. The material was weighed, dissolved in water and normalized to stock concentrations using absorbance measurements at 290 nm versus standards.

PRO 1135 was fractionated in this manner to obtain polymer fractions possessing a peak molecular weight (Mp) of 31 kDa (average molecular weight (MW) -38 kDa); an Mp of 16 kDa (MW -22 kDa); an Mp of 10 kDa (MW -15 kDa); and an Mp of 5.6 kDa (MW -10 kDa).

Light Scattering Methodology

The samples were subjected to analytical HPLC using a Waters 625 pump/modified 410 RI detector that contained inside a PD2000 laser light scattering intensity detector (Precision Detectors, Inc., Amherst, MA). This system was equipped with a Waters Ultrahydrogel 250 aqueous GPC column (7.8 mm I.D.×300 mm, 250 Å pore size, $8×10^4$ exclusion limit, PEO). The mobile phase consisted of 65% 0.2M ammonium acetate pH=6.5/35% acetonitrile in an isocratic mode with a flow rate of 1 ml/min. Elution was monitored by RI, low (15°) and high (90°) angle light scattering and absolute molecular weight ranges were obtained from this information.

Demonstration of Binding to CD4

Fluorescence emission spectra of PRO 1041, PIC 024.4 and fractionation products were recorded using an excitation wavelength of 315 nm as described above. Wild type 2 domain recombinant CD4 (20 μl of a 130 μM stock solution in PBS) was then added to a final concentration of 5 μM and the measurements were repeated. An excitation wavelength of 315 nm ensured that no inner filter effect, nor fluorescence signal, was contributed by the added protein. Furthermore, the low concentrations of the reagents employed excluded significant collisional fluorescence quenching. Therefore, the observation of 60–70% quenching of the fluorescence signals for both PRO 1041 and PIC 024.4 in the presence of CD4 protein, provided evidence for binding to the receptor.

Based on the studies described in this exemplification PIC 024.4 was identified as a naphthalenesulfonic acid formaldehyde condensate, a polymeric dispersant additive to the dye, possessing the identifying characteristics of PRO 1041.

CD4/gp120 Binding Assay: Cellular

CEM cells (a human T-cell leukemia line available from the American Type Culture Collection, Rockville, Md.; $3\times10^6$ cells per ml) were suspended in RPMI 1640 (Whittaker-Bioproducts, Walkersville, MD) with 10% fetal bovine serum (FBS) (JRH Biosciences, Lenexa, KS) plus 0.1% sodium azide. 100 μl of the suspension were added to each tube. Generally, the test compounds were dissolved in water to a final concentration of 4 mg/ml. Various dilutions (1:40, 1:100, 1:200) of PIC 024.4, PRO 1041 or fractionated PRO 1135 were added to the tubes and incubated for 2 hours at 25° C. Next, gp120 (American Bio-Technologies, Inc., Cambridge, Mass.), diluted in RPMI 1640 buffer, was added to a final concentration of 10 nM. The solution was then incubated overnight (~16 hours) at 37° C.

Cells were washed thoroughly with phosphate-buffered saline (PBS) containing 10% FBS and 0.1% sodium azide. To reveal bound gp120, monoclonal antibody specific for gp120 (NEN-Dupont, NEA-9284) was then incubated with the cells at a concentration of 1 μg/ml (100 μl per tube) for 30 minutes on ice. The cells were washed thoroughly as before and stained with goat anti-mouse immunoglobulin (Boehringer Mannhein Biochemicals, Indianapolis, Ind.) which was labeled with fluorescein (50 μl per tube) for 30 minutes on ice. The washed cells were analyzed for fluorescence on a FACScan™(Becton Dickinson).

CD4/qp120 Binding Assay: ELISA

The ELISA (Dupont NEN, Boston, Mass.) utilized a 4domain soluble CD4 (sCD4) purified from Chinese hamster ovary cells which was immobilized to a 96-well microtiter plate. Fifty μl of gp 120 (1 ng at 20 ng/ml) and 50 μl of active compound at appropriate concentrations were added to the microtiter plate in duplicate and incubated overnight at 4° C. The plate was washed 6 times with Wash buffer (2 mg/ml BSA/PBS) and 100 μl anti-gp120 monoclonal antibody-horseradish peroxidase (HRP) conjugate was added. The plate was incubated 2 hours at 4° C., washed 6 times with Wash buffer and developed with 100 μl ortho phenylenediamine (OPD) substrate solution for 30 minutes at 25° C.. A dose-response curve with increasing concentrations of soluble, baculovirus-derived gp120 (HIV-1 IIIB strain) was prepared which illustrated that half-maximal binding occurred at a concentration of 20 ng/ml as detected by HRP-conjugated anti-gp120 monoclonal antibody specific for residues 308–322 on gp120. Therefore, varying concentrations of polymer were incubated in the presence of a constant amount of gp120 (1 ng at 20 ng/ml) to assess inhibition of CD4/gp120 interactions.

The $IC_{50}$ for polymers tested is summarized in Table 2.

TABLE 2

| Polymer | Product size (kDa) | | | $IC_{50}$ (ug/ml) |
|---|---|---|---|---|
| | Mp | MWd | MW | |
| PRO 1041 | 6.0 | 0.7–150 | 16 | 0.05 |
| PRO 1077 | 25 | 0.2–100 | 13 | 0.10 |
| PRO 1078 | 2.0 | 2–200 | 12 | 1.0 |
| PRO 1079 | 0.4 | 0.3–175 | 9 | 1.5 |
| PRO 1080 | 2.0 | 0.4–90 | 9 | 0.9 |
| PRO 1081 | 4.0 | 0.4–100 | 14 | 0.25 |

TABLE 2-continued

| Polymer | Product size (kDa) | | | $IC_{50}$ (ug/ml) |
|---|---|---|---|---|
| | Mp | MWd | MW | |
| PRO 1082 | 8.0 | 3–100 | 14 | 0.10 |
| PRO 1083 | 21 | 0.1–980 | 56 | 0.07 |
| PRO 1121 | 0.2 | 0.2–10 | 2 | 70 |
| PRO 1122 | 0.2 | 0.3–15 | 2 | 20 |
| PRO 1133 | 3.0 | 0.3–100 | 4 | 20 |
| PRO 1135 | 3.0 | 0.3–80 | 14 | 0.55 |
| PRO 1075 | 3.0 | 0.3–100 | 11 | 0.70 |
| PRO 1076 | 4.0 | 1–120 | 18 | 0.18 |

RoSette Inhibition Assay: CD2/LFA-3 (CD58)

Sheep red blood cells (SRBC) (Whittaker-Bioproducts, Walkersville, MD) were pretreated with 2-aminoethyl-isothiouronium bromide (AET, 40 μg/ml) for 15 minutes at 37° C., washed in HANK'S Balanced Salt Solution (HBSS Mediatech) +2.5% FCS, and resuspended to $1.5\times10^9$ cells/ml. Jurkat cells were washed in HBSS +2.5% FCS, and resuspended in the same at a concentration of $1.25\times10^7$ cells/ml. Twenty μl of Jurkat cells were incubated with 20 μl of PIC 024.4 at various concentrations for 30 minutes at 4° C. SRBC ($1.5\times10^7$ in 10 μl) were added to the Jurkat cells, and the cells were incubated together for 5 minutes at room temperature, centrifuged at 300 rpm for 5 minutes, then incubated on ice for 1 hour. Cells were gently resuspended, diluted with HBSS +2.5% FCS and observed in a hemacytometer.

T Cell Proliferation Assays 1. Cells

Mononuclear cells (MNC) were separated from peripheral blood of donors known to be responders to Herpes Simplex Virus (HSV)-i, Rubella, and/or Tetanus toxoid. Whole blood was diluted 1:4 with HBSS, layered over Ficoll-Paque (Pharmacia LKB Biotechnology Inc., Piscataway, NJ) and centrifuged at 1600 rpm for 30 minutes. MNC were washed three times with HBSS, then cultured in medium containing RPMI 1640 supplemented with 5% human AB serum (Flow Labs, McLean, VA), glutamine (2 mM), penicillin/streptomycin, sodium pyruvate and HEPES. For proliferation assays, cells were cultured in 96-well round-bottom microtiter plates in a humidified incubator with 5% $CO_2$ at 37° C. Jurkat cells were maintained in RPMI 1640 plus 10% FCS with supplements described above.

2. Proliferation Assays

To stimulate T cells with viral antigens, $10^5$ MNC/well were cultured with and without inhibitors with dilutions of concentrated culture fluids from HSV-1 or Rubella infected cells vs. control supernatant (SN) from uninfected cells (Microbix Biosystems Inc., Toronto, Ontario). SN contained virus inactivated by gamma radiation. HSV-1 cultures were pulsed with $^3$H-thymidine (TdR) on Day 3, and harvested on Day 4. Rubella cultures were pulsed on Day 5 and harvested on Day 6. MNC from donors immunized against Tetanus toxoid were cultured at $10^5$ /well for 5 days with dilutions of Tetanus toxoid (0.4–4 LF/ml; Massachusetts Department of Public Health, Boston, Mass.).

Cells were pulsed overnight with 1 μCi/well of $^3$H-TdR (ICN, Irvine, Calif.) and harvested onto glass fiber filters using a PHD harvester (Cambridge Technology, Inc., Watertown, Mass.). Thymidine incorporation was measured by liquid scintillation counting using a Pharmacia Beta counter (Pharmacia LKB Nuclear, Inc., Gaithersburg, Md).

Mitomycin-treated MNC or stimulator cells were used in some experiments. Cells were suspended in HBSS at $10^7$/ml and treated with 50 μg/ml of Mitomycin C (Sigma, St. Louis, Mo.) for 30 minutes at 37° C.

To measure T-cell responses to allo-antigens, PBLs were obtained from two MHC-disparate donors. One set of cells were treated with mitomycin c which then served as the stimulator cells. The other set was used as the responder cell population. The cells ($2\times10^5$ per well) were added to microculture wells and were pulsed 4–5 days later with tritiated thymidine as described above, harvested and radioactivity measured.

For the assay of CDS-bearing cells, a T cell line which was specific for Epstein Barr Virus (EBV)-transformed B cells was used. The line was generated from a normal human donor by repeated rounds of stimulation by EBV transformed B cells followed by expansion/rest periods in Interleukin 2 (IL-2). Greater than 80% of the T cells bear CD8 as judged by immunofluorescence. For these studies, the EBV line was treated with mitomycin c to prevent proliferation. T cells ($1\times10^5$) were added to microculture wells and proliferation measured as described above.

Toxicity Testing

To determine whether the compound had general antiproliferative effects (indicative of toxicity), they were tested with the various cell lines Jurkat (T leukemia), K562 (Erythroleukemia), U937 (histiocyte), CEM (T lymphoblast), and RS-EBV (EBV-transformed line). Cells ($5\times10^5$ ml) were incubated in microculture wells with various dilutions of PIC 024.4. Normally, the cells will proliferate spontaneously and this can be measured by evaluating $^3$H-thymidine uptake. After 24 hours, the cells were exposed to 1 μCi of thymidine per well and 16 hours later the plates were harvested and filters counted for radioactivity. For comparison, standard wells were set up that received culture medium only and these wells served as the basis for determining inhibition of thymidine uptake. PIC 024.4 inhibited CEM cell proliferation by 14% at 100 μg/ml and RS-EBV cell proliferation by 27% at 100 μg/ml.

The results of screening PIC 024.4 in the above assays are shown in Table 3, below. FIG. 1 illustrates the results of the CD4/gp120 ELISA assay with PIC 024.4 and PRO 1041. PIC 024.4 and PRO 1041 inhibit the binding of gp120 to CD4 in a dose-dependent manner with an $IC_{50}$ of about 0.2 μg/ml. The results of the Rosette Inhibition assay show no effect of PIC 024.4 on CD2/LFA-3 interactions at doses up to 100 μg/ml. The T cell proliferation assay shows a similar lack of effect at these doses. As shown by the in vitro toxicity testing, PIC 024.4 is not toxic at concentrations where it is active in inhibiting the CD4/gp120 interaction.

TABLE 3

| PIC 024.4 Concentration (ug/ml) | % Inhibition | | | | |
|---|---|---|---|---|---|
| | $CD_4$/gp120 ELISA | Cellular | $CD_2$/$LFA_3$ | T-cell Proliferation | In Vitro Toxicity |
| 100 | — | 99 | 2 | 0 | 3 |
| 40 | — | 97 | 0 | 0 | 0 |
| 20 | — | 89 | 2 | 0 | 0 |
| 10 | 90 | 51 | 0 | — | — |
| 5.0 | — | 27 | — | — | — |
| 2.5 | — | 12 | — | — | — |
| 1.0 | 77 | — | — | — | — |
| 0.1 | 43 | — | — | — | — |
| 0.01 | 2 | — | — | — | — |

Antiviral activity and cytotoxicity assay employing HTLVIIIB:

PIC 024.4 was dissolved in sterile water at a concentration of 4 mg/ml. Dilutions were prepared in culture medium, and the compound was tested at concentrations ranging from 100 μg/ml to 0.003 μg/ml in half-$\log_{10}$ dilutions.

The assay was done in 96-well tissue culture plates using the CEM-T4 human T-lymphocyte cell line. The culture medium used was RPMI-1640 medium containing 25 mM N-[2-Hydroxyethyl]piperazine-$n^1$-[2-ethanesulfonic acid] (HEPES, Sigma Chemical Co.) and 2 mM L-glutamine, and supplemented with 10% fetal bovine serum, 2 mM L-glutamine, 50 units of penicillin G per ml, and 50 μg streptomycin sulfate per ml. CEM-T4 cells were treated with polybrene at a concentration of 2 μg/ml, and a 130 μl volume of cells ($1\times10^4$ cells) was dispensed into each well. To one assay plate for each drug a 50 μl volume of each drug dilution (prepared as a 4×concentration) was added to five wells of cells, and the cells were incubated at 37° C. for two hours. This resulted in the pre-treatment of the cells with drugs at a 1.1× concentration. A second assay plate for each drug, containing just the dispensed cells, was incubated in parallel.

For all assay plates, a frozen culture of HIV-1, strain HTLV-III$_B$, was diluted in culture medium to a concentration of $2.5\times10^4$ TCID$_{50}$ per ml, and a 20 μl volume (containing 500 TCID$_{50}$ of virus) was added to three wells for each drug concentration. This resulted in a multiplicity of infection of 0.05 for the HIV-1 infected samples. A 20 μl volume of normal culture medium was added to two wells for each drug concentration to allow evaluation of drug cytotoxicity.

After a two hour incubation with virus at 37° C., a 50 μl volume of each drug dilution (prepared as a 4× concentration) was added to three infected wells of cells and to two uninfected wells of cells for the second assay plate of each drug.

Each assay plate contained five wells of untreated, uninfected, cell control samples and five wells of untreated, infected, virus control samples. 2', 3'-Dideoxyinosine (DDI) was assayed in parallel using both protocols for drug addition.

The tissue culture plates were incubated at 37° C. in a humidified, 5% $CO_2$ atmosphere and observed microscopically for toxicity and/or cytopathogenic effect. On the eighth day post-infection, the cells in each well were suspended and a 50 μl sample of each cell suspension was transferred to a new 96-well plate for use in the following assay. A 100 μl volume of fresh RPMI-1640 medium and a 30 μl volume of a 5 mg/ml solution of 3-(4,5-dimethylthiazol-2-yl)-2,5-diphenyltetrazolium bromide (MTT) were added to each 50 μl cell suspension, and the cells were incubated at 37° C. in 5% $CO_2$ for four hours. During this incubation MTT is metabolically reduced by living cells, resulting in the production of a colored formazan product. A 50 μl volume of a solution of 20% sodium dodecyl sulfate in 0.02 N hydrochloric acid was added to each sample, and the samples were incubated overnight. The absorbance at 590 nm was determined for each sample using a Molecular Devices $V_{max}$ microplate reader. This assay detects drug-induced suppression of viral cytopathic effect (CPE), as well as drug cytotoxicity, by measuring the generation of MTT-formazan by surviving cells. When a dose-dependent effect for either CPE-inhibition or toxicity was seen, values for the 50% effective dose were calculated using the dose effect analysis software of Chou and Chou (ElsevierBiosoft).

The results are summarized in Table 4.

In vitro Anti-HIV Assay and Cytotoxicity Assay Employing Strain JR-CSF:

The purpose of this procedure is to look at the toxicity and effect of a compound on free HIV virus infection of human phytohemagglutinin (PEA) blasts, in vitro, for a virus isolate (JR-CSF) which has previously been shown to be resistant to therapy with recombinant soluble CD4 (sCD4). The day before setting up an assay, human PHA activated T cell blasts were thawed from liquid nitrogen and cultured overnight in Iscove's Modified Dulbecco Medium (IMDM) plus 7% FCS and 50 units/ml IL-2 at a density of $10^6$/ml.

PHA activated T cell blasts were pelleted and resuspended at $4\times10^6$ per ml in medium containing 7% FCS and 50 units/ml IL-2. Twenty-five μl of the cell suspension were plated per well in round bottom 96 well microtiter plates ($10^5$/well) and placed in a 37° C. incubator. Twenty-five μl of the compound to be tested at appropriate dilutions in 7% FCS/IMDM containing 50 units/ml IL-2 (2× the final concentration) or tissue culture medium alone (as a negative control) were added to the cells and incubated for 2 hours at 37° C. Two hundred μl of medium was added and the test compound was washed out by centrifugation of the 96 well plates for 2 minutes at 1000 rpm and aspiration of 250 μl. The cells were resuspended in 50 μl medium containing 7% FCS and 50 units/ml IL-2. HIV (JR-CSF, Koyanagi et al., *Science*, 236:819–821 (1987)) was diluted to 50 $TCID_{50}$ (in 25 μl) in IMDM containing 7% FCS and 50 units/ml IL-2 plus polybrene (10 μg/ml) in 24 well plates. Twenty-five μl of virus were added per well to the cells. HIV infection was allowed to proceed for 2 hours at 37° C., followed by addition of 200 μl of medium. The virus was washed out by centrifugation of the 96 well plates for 2 minutes at 1000 rpm, aspiration of 250 μl, and addition of 200 μl of fresh medium containing 7% FCS and 50 units/ ml IL-2 and the appropriate amount of test compound (1×). Medium was removed and replaced with fresh medium containing 7% FCS and 50 units/ml IL-2 plus test compound (1×) on day 4. On day 7, the plates were centrifuged at 1000 rpm for 5 minutes, and supernatants were carefully removed from each well. The cells were lysed and assayed for p24 antigen at a 1:35 dilution.

Percent inhibition was determined relative to untreated, infected control cells. For instance, if the amount of p24 antigen in control well is A and the amount of p24 in a well with a test compound is B, then the compound achieves (A-B/A)(100) % inhibition of that concentration.

In establishing toxicity, PHA activated T cell blasts were pelleted and resuspended at $2\times10^6$ per ml and plated in 96 well round bottom microtiter plates at $10^5$ per well (50 μl) in IMDM plus 7% FCS and 50 units/ml IL-2. Twenty-five μl of the compound to be tested at appropriate dilutions in 7% FCS/IMDM containing 50 units/ml IL-2 (3× the final concentration) or tissue culture media alone (controls) was added to the 96 well plate. This mixture was incubated for 2 hours at 37° C., followed by addition of 200 μl of medium. The test compound was washed out by centrifugation of the 96 well plate(s) for 2 minutes at 1000 rpm, aspiration of 250 μl and addition of 200 μl of fresh medium containing IL-2 and the appropriate amount of test compound (1×). Medium was removed and replaced with fresh medium containing test compound on day 4.

At day 7, the appropriate number of cells (100 μl) was transferred to another plate. Toxicity of the test compounds was assayed by the MTT assay, substantially as described above.

Analysis of AZT indicated no cytotoxicity in the concentration range of 0.0004–50 μM. p24 levels were substantially reduced in the anti-HIV assay using JR-CSF at concentrations of 0.004–50 μM where the drug was added 2 hours prior to infection. Anti-HIV activity was clearly demonstrated for this compound. The results achieved were in the range of expected values obtained from previous assays.

Analysis of PIC 024.4 indicated slight cytotoxicity at only the highest concentration tested: 100 μg/ml. p24 levels were substantially reduced in the anti-HIV assay using JR-CSF and concentrations of PIC 024.4 equal to 100, 20, and 4 μg/ml where the drug was added 2 hours prior to infection. Anti-HIV activity was clearly demonstrated for this compound with activity observed at a concentration 25-fold below that where toxicity was observed.

Figure 2:
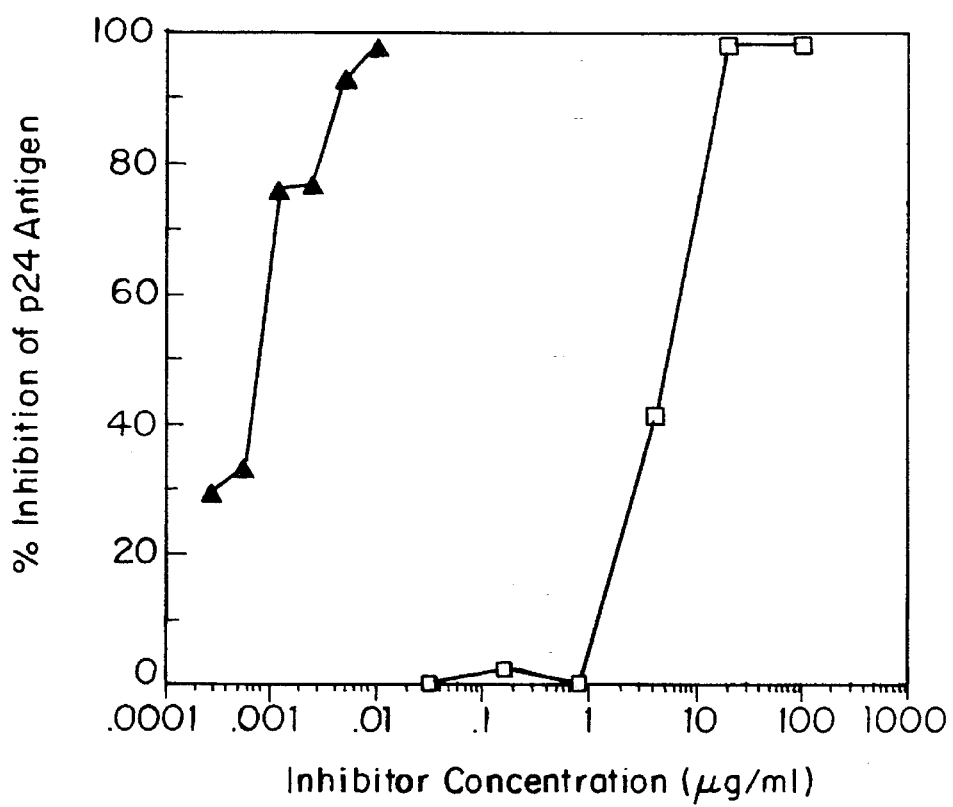
FIG. 2 is a graph of an in vitro anti-HIV activity of PIC 024.4 (designated by an open square) and AZT (designated by a closed diamond) against HIV (strain JR-CSF).

The results are summarized in Table 4 and illustrated in FIG. 2.

Human Monocyte-Macrophage Studies with HIV-1 (ADA): Assays of HIV Infection of Monocyte Targets Human peripheral blood leukocytes were obtained by countercurrent centrifugal elutriation and the monocytes allowed to adhere to the surface of tissue culture flasks. The monocytes were cultured as an adherent monolayer for 7-days in DMEM supplemented with 10% heat-inactivated human $AB^+$serum, 50 μg/ml gentamycin, and 1,000 units/ml macrophage colony stimulating factor (mCSF, Cetus). Preincubation in mCSF was performed because it markedly increases (7 to 10 fold) HIV-1 expression in vitro. After pre-incubation, the cell population harvested by scraping was shown to contain >98% monocytes using cell morphology on Wright-stained cytosmears, and histochemical staining for granular peroxidase and nonspecific esterase. The monocytes at a concentration of $1\times10^6$/ml were then added to the wells of 24-well plates and allowed to form adherent monolayers. Prior to infection with HIV-1, the media was aspirated carefully from each well. The plates were washed carefully three times with 37° C. PBS to remove all residual serum. Thirty to fifty μl/well of $HIV_{ADA}$ strain (D. Chester Kalter et al., *J. Immunol.* J46:298–306 (1992)) in 70-50 μl RPMI (this represents 3.0 $\log_{10}$ $TCID_{50}/10^5$ cells) was added, and incubated for at least 2 hours at 37° C. Compounds were added in 10% FCS RPMI with mCSF (C-34) at 1,000 units/ml to the plates. Controls included: + cells + virus; + cells − virus; and − cells + virus. O n day 7, the supernatant was removed as follows: 1 ml for reverse transcriptase, 0.5 ml for p24 assay, and the medium was replenished with fresh drug. The final harvest was on day 14.

Figure 3:
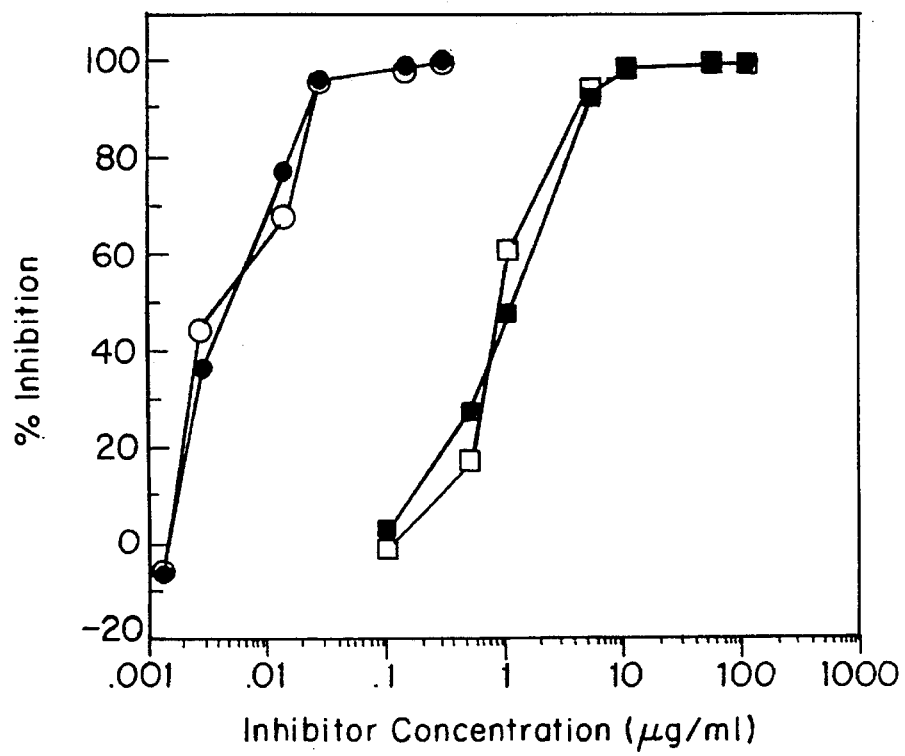
FIG. 3 is a graph of in vitro anti-HIV (strain ADA) activities at Days 7 and 14 of PIC 024.4 (designated by an open square at Day 7 and a closed square at Day 14) and AZT (designated by a open circle at Day 7 and a closed circle at Day 14).
Figure 4:
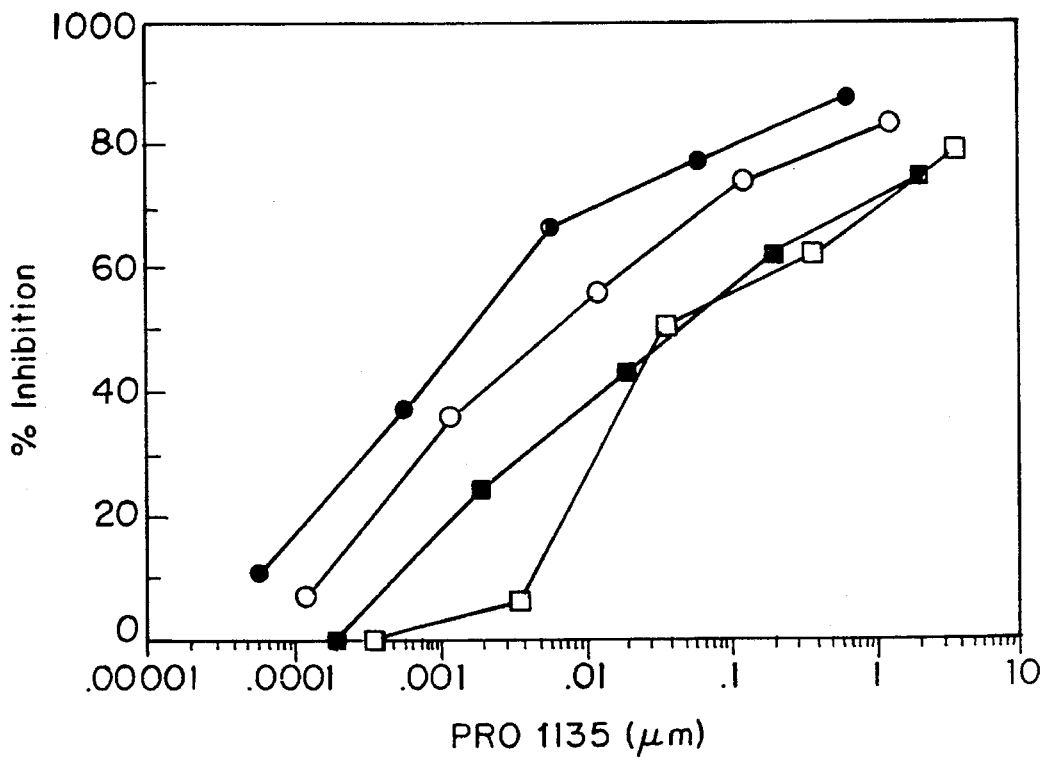
FIG. 4 is a graphic illustration of the size/ activity relationship of fractions of PRO 1135 possessing a peak molecular weight of 5.6 kDa (open square), 10 kDa (closed square), 16 kDa (open circle) and 31 kDa (closed circle) in the inhibition of gp120 binding to sCD4 (Elisa).
Figure 5:
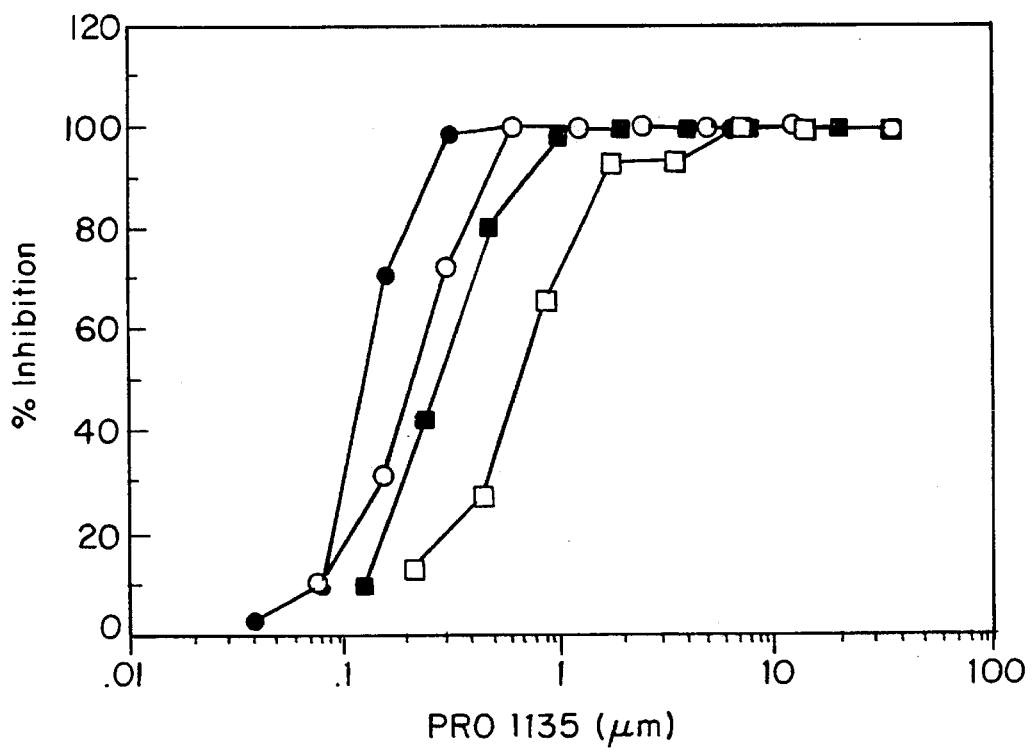
FIG. 5 is a graph of the size/activity relationship of fractions of PRO 1135 possessing a peak molecular weight of 5.6 kDa (open square), 10 kDa (closed square), 16 kDa (open circle) and 31 kDa (closed circle) in the inhibition of gp120 binding in the CD4/gp120, binding assay: cellular.
Figure 6:
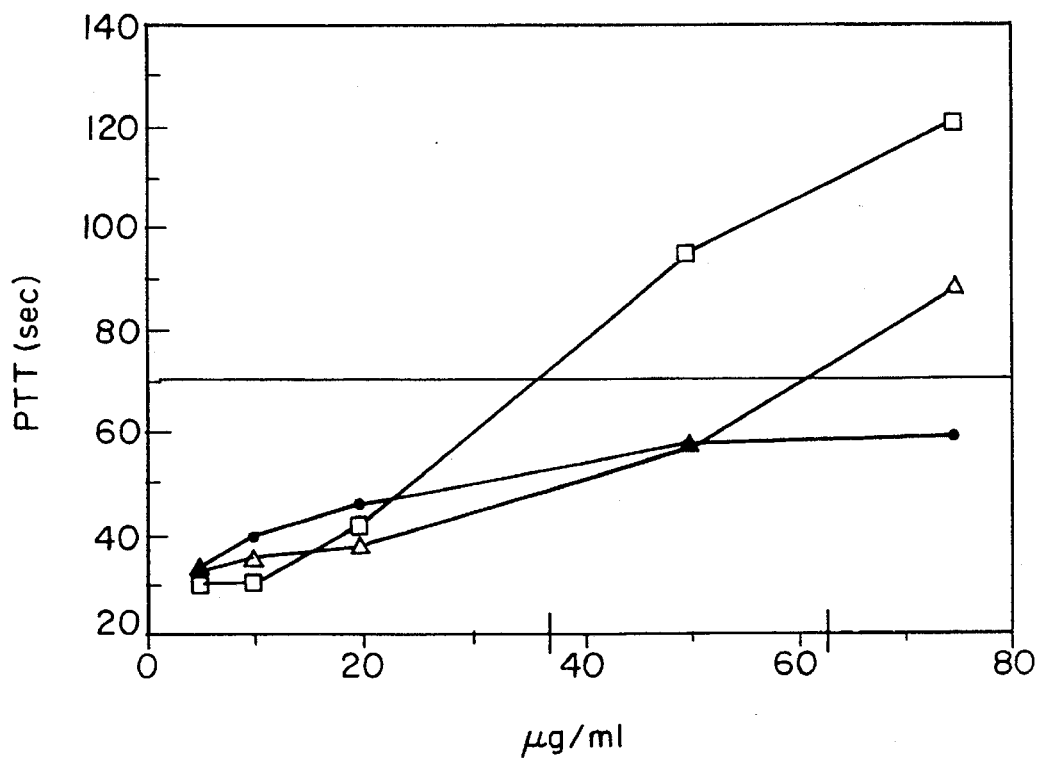
FIG. 6 is a graphic illustration of the anticoagulation activity of the 31 kDa (open square), 10 kDa (closed square) and 5.6 kDa (closed diamond) fraction of PRO 1135.
Figure 8:
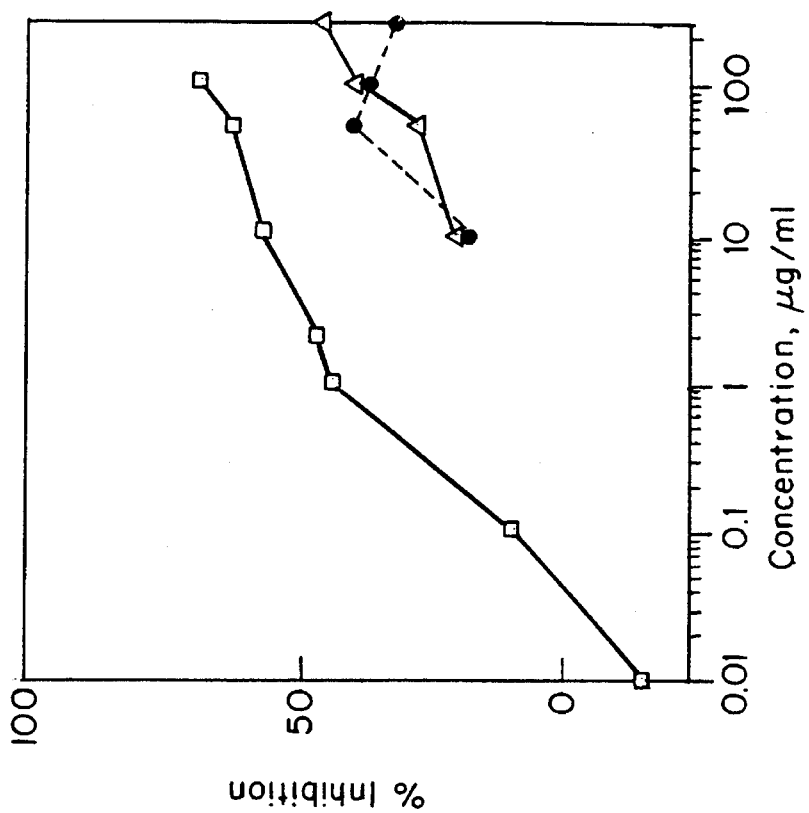
FIG. 8 is a graphic illustration of the Elisa assay for inhibition of CD4-gp120 binding for PRO 1191 (octamer, open square), PRO 1072 (tetramer, open diamond) and PRO 1073 (hexamer, open circle) of the formaldehyde-2-naphthalenesulfonic acid condensate oligomer.
Figure 7:
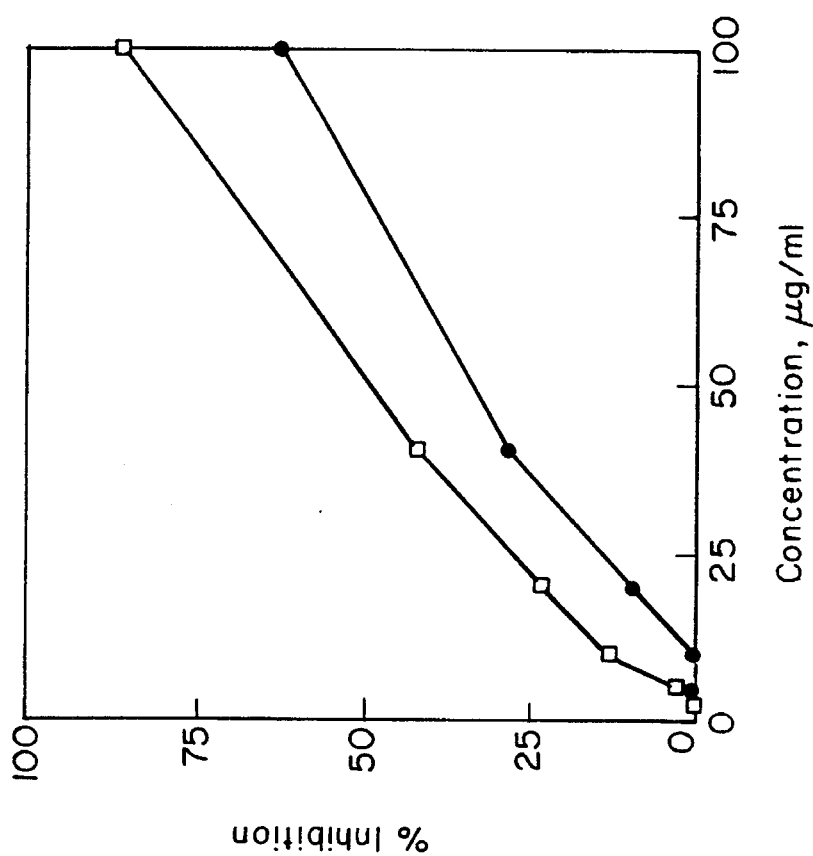
FIG. 7 is a graphic illustration of the inhibition of gp120 binding to CD4 in the cellular assay for PRO 1191 (octamer, open square) and PRO 1072 (tetramer, open diamond) of the formaldehyde - 2-naphthalenesulfonic acid condensate oligomer. PRO 1191 and PRO 1072 exhibited an $ICs_{50}$ of 52 and 78, respectively.

The results are summarized in Tables 4 and 5 and illustrated in FIG. 3.

TABLE 4

| Compound | Antiviral Activity $ID_{50}$ (μg/ml) | | | Cytotoxicity $TD_{50}$ (μg/ml) | |
|---|---|---|---|---|---|
| | $III_B$ | JR-CSF | ADA | CEM-T4 ($III_B$) | T-Blasts (JR-CSF,ADA) |
| PIC 024.4 | 8.4 | ≈4 | 1.0 | >100 | >100 |
| ddI | 1.2 | | | >25 | |
| AZT | | 0.001 | 0.005 | | >10 |
| Dextran Sulfate* | | | | | |
| AHT 8 | 8 | | | | |
| TM 11 | 4 | | | | |

*(Science, 240:646–649, 1988)

TABLE 5

| Drug | EC50 (μg/ml) | | EC90 (μg/ml) | |
|---|---|---|---|---|
| | Day 7 | Day 14 | Day 7 | Day 14 |
| PIC 024.4 | 1.02 | 0.93 | 3.17 | 3.48 |
| AZT | 0.005 | 0.003 | 0.02 | 0.01 |

Anticoagulation Assay: Activated Partial Thromboplastin Time Assay

Venous blood (9.0 ml) was added to 1 ml of 3.9% sodium citrate (ratio of 1:10) in a top vacutainer tube and immediately centrifuged. This step removed calcium, a required factor in coagulation- The specimen was free of hemolysis and clots.

A tube of 0.02M calcium chloride solution was placed in the back of a Fibrometer heating block and allowed to reach about 37° C. Activated Cephaloplastin (0.1 ml, Dade) was mixed well and pipetted into three coagulation cups. The cups were warmed for about one minute at 37° C.

One ml of the above citrated plasma was incubated with the test compound for about 60 minutes at about 37° C. The incubated plasma (0.1 ml) was added to the first cup of cephaloplastin. At the end of the second minute, 0.1 ml of plasma was added to the second cup. At the end of the third minute, 0.1 ml of plasma was added to the third cup. After the addition of plasma to each cup, the contents were mixed well and incubated at about 37° C. for about 3 minutes each.

The cups of plasma-cephaloplastin mixture were then placed under the Fibrometer probe and 0.1 ml of the 0.02 m calcium chloride was added. The time (the partial thromboplastin time, PTT) necessary to result in clotting was then measured. Normal values for PTT are, generally, between about 30 to 45 seconds.

EQUIVALENTS

Those skilled in the art will recognize, or be able to ascertain, using no more than routine experimentation, many equivalents to the specific embodiments of the invention described specifically herein. Such equivalents are intended to be encompassed in the scope of the following claims:

We claim:

1. A method of inhibiting HIV infection in an individual comprising administering to the individual an effective amount of an antiviral composition comprising a condensation polymer of an aromatic sulfonic acid and an aldehyde or salt thereof in a physiologically acceptable carrier.

2. The method of claim 1 wherein the antiviral composition is administered intravaginally or rectally.

3. The method of claim 2 wherein the physiologically acceptable carrier is a contraceptive formulation.

4. The method of claim 3 wherein the physiologically acceptable carrier is a contraceptive gel, cream or foam.

5. The method of claim 1 wherein the antiviral composition is administered parenterally.

6. A method of treating HIV infection in an HIV-infected individual comprising administering to the individual an effective amount of an antiviral composition comprising a condensation polymer of an aromatic sulfonic acid and an aldehyde or salt thereof in a physiologically acceptable carrier.

7. The method of claim 6 wherein the antiviral composition is administered parenterally.

8. The method of claim 6 wherein the condensation polymer is a condensation polymer of a naphthalene sulfonic acid and formaldehyde.

9. The method of claim 8 wherein the condensation polymer is a compound having the identifying characteristics of PRO 1041.

10. The method of claim 8 wherein the condensation polymer has a peak molecular weight of less than about 50 kDa.

11. The method of claim 10 wherein the condensation polymer has a peak molecular weight between from about 0.7 kDa and about 50 kDa.

12. The method of claim 11 wherein the condensation polymer has a peak molecular weight between from about 1.3 kDa to about 30 kDa.

13. The method of claim 12 wherein the condensation polymer has a peak molecular weight between from about 4 kDa to 12 kDa.

14. The method of claim 8 wherein the condensation polymer has an average of between about 0.5 to about 2.0 sulfonic acid groups per aromatic group.

15. The method of claim 14 wherein the condensation polymer has an average of about 1 sulfonic acid group per aromatic group.

16. The method of claim 8 wherein the condensation polymer has a therapeutic ratio of at least about 7.

17. The method of claim 16 wherein the condensation polymer has a therapeutic ratio of at least about 20.

18. A method of claim 8 wherein the physiologically acceptable carrier is a contraceptive formulation.

19. A method of inhibiting HIV infection comprising contacting the HIV virus with an effective amount of an antiviral composition comprising a condensation polymer of an aromatic sulfonic acid and an aldehyde or salt thereof in a physiologically acceptable carrier.

20. The method of claim 19 wherein the physiologically acceptable carrier is a contraceptive formulation.

21. The method of claim 20 wherein the physiologically acceptable carrier is a contraceptive gel, cream or foam.

22. A method of claim 19 wherein the condensation polymer is a condensation polymer of a naphthalenesulfonic acid and formaldehyde.

23. A method of claim 22 wherein the condensation polymer is a compound having the identifying characteristics of PRO 1041.

24. The method of claim 22 wherein the condensation polymer has a peak molecular weight of less than about 50 kDa.

25. The method of claim 24 wherein the condensation polymer has a peak molecular weight between from about 0.7 kDa and about 50 kDa.

26. The method of claim 25 wherein the condensation polymer has a peak molecular weight between from about 1.3 kDa to about 30 kDa.

27. The method of claim 26 wherein the condensation polymer has a peak molecular weight between from about 4 kDa to 12 kDa.

28. The method of claim 22 wherein the condensation polymer has an average of between about 0.5 to about 2.0 sulfonic acid groups per aromatic group.

29. The method of claim 28 wherein the condensation polymer has an average of about 1 sulfonic acid group per aromatic group.

30. The method of claim 22 wherein the condensation polymer has a therapeutic ratio of at least about 9.

31. The method of claim 30 wherein the condensation polymer has a therapeutic ratio of at least about 20.

32. A method of claim 22 wherein the physiologically acceptable carrier is a contraceptive formulation.

33. A method of inhibiting HIV infection binding in a blood preparation, comprising adding to said blood preparation an effective amount of a composition comprising a condensation polymer of an aromatic sulfonic acid and an aldehyde in a physiologically acceptable carrier.

34. A method of claim 33 wherein the condensation polymer is a condensation polymer of a naphthalenesulfonic acid and formaldehyde.

35. A method of claim 34 wherein the condensation polymer is a compound having the identifying characteristics of PRO 1041.

36. The method of claim 33 wherein the condensation polymer has a peak molecular weight of less than about 50 kDa.

37. The method of claim 36 wherein the condensation polymer has a peak molecular weight between from about 0.7 kDa and about 50 kDa.

38. The method of claim 37 wherein the condensation polymer has a peak molecular weight between from about 1.3 kDa to about 30 kDa.

39. The method of claim 38 wherein the condensation polymer has a peak molecular weight between from about 4 kDa to 12 kDa.

* * * * *

UNITED STATES PATENT AND TRADEMARK OFFICE
CERTIFICATE OF CORRECTION

PATENT NO. : 5,614,559
DATED : March 25, 1997
INVENTOR(S) : Singh et al.

It is certified that error appears in the above-indentified patent and that said Letters Patent is hereby corrected as shown below:

Column 16, line 60, Claim 33, after the word infection delete "binding".

Signed and Sealed this

Twenty-eighth Day of October, 1997

Attest:

BRUCE LEHMAN

Attesting Officer

Commissioner of Patents and Trademarks